(12) United States Patent
Frehner et al.

(10) Patent No.: US 8,980,335 B2
(45) Date of Patent: Mar. 17, 2015

(54) USE OF ORGANIC ACIDS AND ESSENTIAL OILS IN ANIMAL FEEDING

(75) Inventors: Marco Frehner, Mout-sur-Rolle (CH); Christophe Paulus, Colmar (FR); Petra Philipps, Grenzach-Wyhlen (DE); Martin Gadient, Basel (CH)

(73) Assignee: DSM IP Assets B.V., Heerlen (NL)

(*) Notice: Subject to any disclaimer, the term of this patent is extended or adjusted under 35 U.S.C. 154(b) by 1179 days.

(21) Appl. No.: 12/146,132

(22) Filed: Jun. 25, 2008

(65) Prior Publication Data
US 2009/0004308 A1  Jan. 1, 2009

(30) Foreign Application Priority Data
Jun. 29, 2007 (EP) .................... 07012784

(51) Int. Cl.
| A61K 36/00 | (2006.01) |
| A23K 1/18 | (2006.01) |
| A23K 1/16 | (2006.01) |
| A61K 31/05 | (2006.01) |
| A61K 31/192 | (2006.01) |
| A61K 31/433 | (2006.01) |

(52) U.S. Cl.
CPC .............. *A23K 1/1826* (2013.01); *A23K 1/1612* (2013.01); *A23K 1/1625* (2013.01); *A23K 1/1813* (2013.01); *A23K 1/184* (2013.01); *A61K 31/05* (2013.01); *A61K 31/192* (2013.01); *A61K 31/433* (2013.01)
USPC .......................................... 424/725; 424/756

(58) Field of Classification Search
None
See application file for complete search history.

(56) References Cited

U.S. PATENT DOCUMENTS

| 5,817,295 | A | * | 10/1998 | Chaudhari et al. ............... 424/49 |
| 2005/0266052 | A1 | * | 12/2005 | Bartlett et al. ................ 424/442 |
| 2006/0008533 | A1 | | 1/2006 | Habich et al. |
| 2008/0032021 | A1 | | 2/2008 | Faltys et al. |

FOREIGN PATENT DOCUMENTS

| JP | 2002-536984 | | 11/2002 |
| JP | 2006-523094 | | 10/2006 |
| WO | WO 9959430 | * | 11/1999 |

OTHER PUBLICATIONS

MSDS for Benzoic acid, Safety Emporium, pp. 1-6, May 25, 2004.*
Bridges et al, "The fate of Benzoic Acid in Various Species", Biochem.J. (1970) 118, 47-51.
Józefiak et al., "The effects of benzoic acid supplementation on the performance of broiler chickens", J. Animal Physiology and Animal Nutrition, 94 (2010) 29-34.

* cited by examiner

*Primary Examiner* — Qiuwen Mi
(74) *Attorney, Agent, or Firm* — Nixon & Vanderhye P.C.

(57) ABSTRACT

The present invention relates to a novel feed composition for animals, for example poultry, comprising as active ingredient benzoic acid, derivatives or metabolites thereof, in combination with a mixture of at least two active compounds selected from the group consisting of thymol, eugenol and piperine. The inventors found that in addition to the well known function of benzoic acid, this compound can be used as a potential growth promoter when it is combined with a mixture of at least two active compounds selected from the group consisting of thymol, eugenol and piperine. In particular the inventors have been able to demonstrate that a mixture of these chemical compounds present in different parts of plants, used in synergy and in combination with an appropriate amount of benzoic acid, exhibits, in totally unexpected manner, the effects sought by the present invention of improving the digestibility of poultry feed, i.e. for improving feed conversion ratio and/or daily weight gain in animal.

10 Claims, 1 Drawing Sheet

USE OF ORGANIC ACIDS AND ESSENTIAL OILS IN ANIMAL FEEDING

CROSS REFERENCE TO RELATED APPLICATION

This application claims the benefit of priority from European Application No. 07012784.0, filed Jun. 29, 2007, the entire content of which is hereby incorporated by reference.

FIELD

The present invention relates to the use of benzoic acid, derivatives or metabolites thereof in combination with a mixture of at least two essential oil compounds selected from the group consisting of thymol, eugenol and piperine for the improvement of the feed conversion ratio and/or weight gain and/or gut flora modulation and for a better health status of the animals.

BACKGROUND AND SUMMARY

The present invention also relates to a novel feed composition for animals, especially poultry, comprising as active ingredient an organic acid, preferably benzoic acid, derivatives or metabolites thereof, in combination with at least one essential oil compound, preferably with a mixture of at least two essential oil compounds selected from the group consisting of thymol, eugenol and piperine.

More particularly, this invention relates to the use of a composition as defined above as a component of animal feed or drinking water or feed or drinking water additives, as well as to compositions, feed additives, drinking water and feed containing them.

Benzoic acid is commercially available (for example as VevoVitall®, supplied by DSM Nutritional Products, Kaiseraugst, Switzerland) or can easily be prepared by a skilled person using processes and methods well-known in the prior art.

The essential oil compounds according to the invention are commercially available or can easily be prepared by a skilled person using processes and methods well-known in the prior art.

The essential oil compounds can be used in highly purified forms in mixtures or in the form of natural available plant extracts or extract-mixtures.

The term "extract" as used herein includes compositions obtained by solvent extraction (which are also known as "extracted oils"), steam distillation (which are also known as "essential oils") or other methods known to the skilled person. Suitable extraction solvents include alcohols such as ethanol.

By the expression "natural" is in this context understood a substance which consists of compounds occurring in nature and obtained from natural products or through synthesis. The natural substance may preferably contain at least two of the compounds as defined above as main ingredient and additionally other essential oil compounds as for example capsaicin, tannin or carvacrol.

The term feed or feed composition means any compound, preparation, mixture, or composition suitable for, or intended for intake by an animal.

The term animal includes all animals including human. Examples of animals are non-ruminants, and ruminants. Ruminant animals include, for example, animals such as sheep, goat, and cattle, e.g. cow such as beef cattle and dairy cows. In a particular embodiment, the animal is a non-ruminant animal. Non-ruminant animals include horses, rabbits; pig or swine (including, but not limited to, piglets, growing pigs, and sows) and poultry such as turkeys, ducks and chickens (including but not limited to broiler chicks, layers).

It is known from EP-A-0 683 985 that animal feed compositions comprising benzoic acid or salts thereof can be used to minimize the emission of odoriferous ammonia from organic wastes in pig farms, especially animal excrements and manure. It is further known that addition of benzoic acid to the diet of weaner piglets improves the zootechnical performance of the animals.

The disadvantage of the use of benzoic acid in animal feeding is, that benzoic acid cannot be used in dosages >10000 mg/kg pig feed and in dosages >5000 mg/kg poultry feed because of undesired adverse effects.

It has now been found surprisingly that the dosage ranges of benzoic acid and salts thereof in the final animal feed can be reduced without losing effectiveness when it is combined with a mixture of active compounds as defined above.

DETAILED DESCRIPTION

Figure 1:
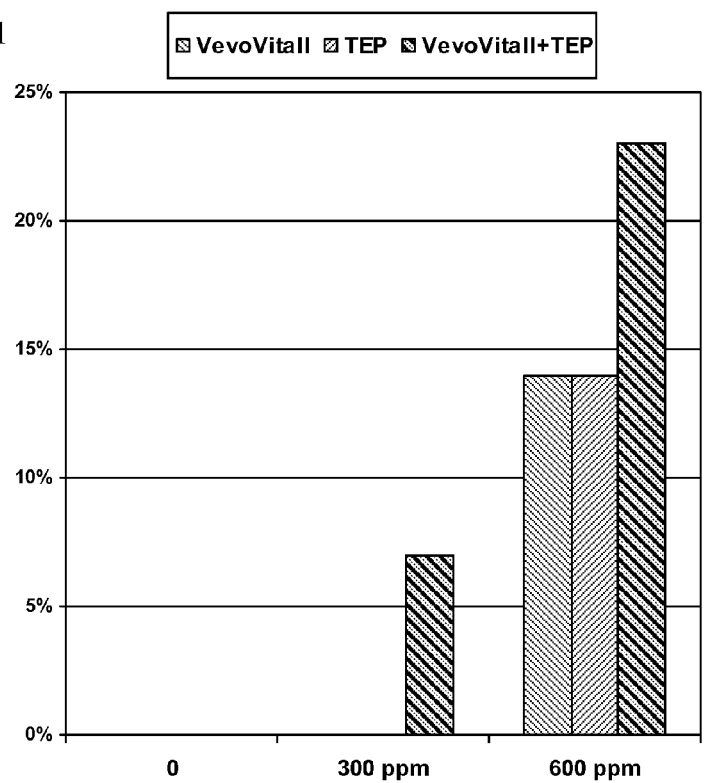
FIGS. 1 and 2 are graphs of the results from Example 4 below wherein data for "Growth inhibition (% of control)" of *Clostridium* perfringens and *Escherichia coli*, respectively, are plotted versus "Content of compound indicated as equivalent contents of the total mixture of the invention".
Figure 2:
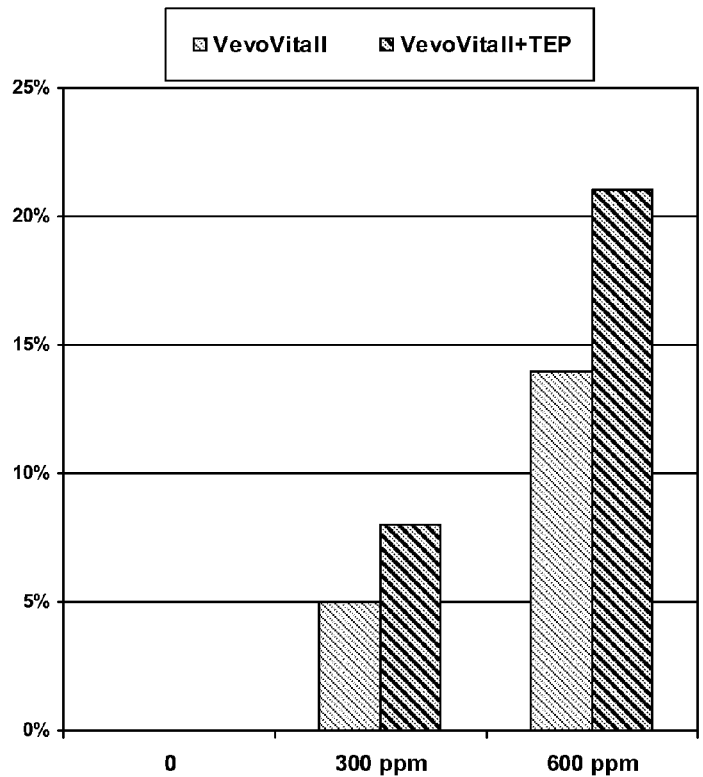

It has been found that in addition to the above function, benzoic acid, a derivative or metabolite thereof can be used as a potential growth promoter when it is combined with a mixture of at least two active compounds selected from the group consisting of thymol, eugenol and piperine. In particular the inventors have been able to demonstrate that a mixture of these chemical compounds, present in different parts of plants, used in synergy and in combination with an appropriate amount of benzoic acid, exhibits, in totally unexpected manner, the effects sought by the present invention of improving the digestibility of poultry feed or of zootechnical performance of animals.

Therefore, this invention relates to the use of benzoic acid, derivatives or metabolites thereof in combination with a mixture of at least two active compounds selected from the group consisting of thymol, eugenol and piperine for the improvement of the feed conversion ratio or weight gain, for example daily weight gain (DWG) in animals. This aspect encompasses also a method of co-feeding of an animal with a composition comprising as main ingredient benzoic acid together with a composition comprising a mixture of at least two compounds selected from the group consisting of thymol, eugenol and piperine.

The term feed conversion ratio is determined on the basis of a growth trial comprising a first treatment in which the composition according to the invention is added to the animal feed in a suitable concentration per kg feed, and a second treatment (control) with no addition of the composition to the animal feed.

As it is generally known, an improved FCR is lower than the control FCR. In particular embodiments, the FCR is improved (i.e. reduced) as compared to the control by at least 1.0% or 5%.

A second aspect of the present invention relates to the use of compositions comprising benzoic acid, a derivative or a metabolite thereof and a mixture of at least two compounds selected from the group consisting of thymol, eugenol and piperine, preferably for the improvement of the feed conversion ratio in animals or DWG.

The present inventors surprisingly found that a feed composition comprising benzoic acid and a mixture of at least two compounds selected from the group consisting of thymol, eugenol and piperine has also unexpected antimicrobial activity and furthermore the potential to modulate the gut flora of the animal.

It is therefore a third object of the present invention to provide the use of benzoic acid, derivatives or metabolites thereof in combination with a mixture of at least two active compounds selected from the group consisting of thymol, eugenol and piperine for modulation of the gut flora of the animal and as antimicrobial agent.

The term "gut" as used herein designates the gastrointestinal or digestive tract (also referred to as the alimentary canal) and it refers to the system of organs within multicellular animals which takes in food, digests it to extract energy and nutrients, and expels the remaining waste.

The term gut "microflora" as used herein refers to the natural microbial cultures residing in the gut and maintaining health by aiding in proper digestion and/or supporting immune system function.

The term "modulate" as used herein in connection with the gut microflora generally means to change, manipulate, alter, or adjust the function or status thereof in a healthy and normally functioning animal, i.e. a non-therapeutic use. The modulation is in response to compositions of the invention.

Antimicrobial activity may, e.g., be bactericidal, bacteriostatic, fungicidal, fungistatic, and/or virucidal. The term "bactericidal" is to be understood as capable of killing bacterial cells; the term "bacteriostatic" as capable of inhibiting bacterial growth, i.e. inhibiting growing bacterial cells; the term "fungicidal" as capable of killing fungal cells; the term "fungistatic" as capable of inhibiting fungal growth, i.e. inhibiting growing fungal cells; and the term "virucidal" is to be understood as capable of inactivating viruses.

The following are non-limiting particular examples of the gut microflora modulation effect obtained by the composition according to the invention (changes as compared to a control without the composition of the invention):
(i) a decrease in the frequency with which *Salmonella* spp and/or *Clostridium perfringens* occurs in vivo, for example in piglets or in broilers;
(ii) a decrease in the number of *Escherichia coli* and/or *Enterococcus faecalis* and/or *Lactobacillus* spp. and/or *Campylobacter* spp in vivo, for example in piglets and/or broilers.

Still further, also in relation to the gut microflora modulating effect, the composition of the invention preferably:
(iii) does substantially influence, e.g. reduce, the growth in vitro of harmful micro-organisms, such as bacteria, for example as isolated from piglet and/or broiler intestinal contents.

A fourth aspect of the invention relates to an animal feed composition or to an additive or a premix therefore, which comprises benzoic acid, a derivative or a metabolite thereof and a mixture of at least two compounds selected from the group consisting of thymol, eugenol and piperine. The amount of benzoic acid or of a derivative thereof administered to the animal is in the range from 0.001-5% based on the total weight of each feed fed to the animal. This amount may, however, be higher if the function of benzoic acid or a derivative thereof is also to control the pH of the animal excreta fed on such a diet in order to suppress the emission of ammonia from the excreta. Such higher amounts are suitably limited to a maximum of about 10% based on the total animal feed composition.

In a preferred embodiment of a poultry feeding concept, benzoic acid or a derivative of benzoic acid being used in an amount sufficient to provide a daily dosage of 5 mg per kg body weight to about 80 mg per kg body weight, preferably 10 mg per kg body weight to about 40 mg per kg body weight, of the subject to which it is to be administered.

The amount of benzoic acid or of a derivative thereof in the final animal feed is in the range from 50 to 1000 mg/kg feed, preferably in the range of 100 to 500, most preferably in the range of 200 to 250 mg kg feed.

It is at present contemplated that the three active compounds thymol, eugenol and piperine are administered in amounts (dosage ranges) of 0.1 to 20 mg per kg feed (ppm), preferably in the range of 0.3 to 10 mg per kg feed.

Examples of particularly preferred dosages of the three compounds in a final poultry feed are independently from each other in the following ranges:
thymol between 1 and 20 ppm, preferably between 1 and 10 ppm;
eugenol between 1 and 5 ppm, for example 2 ppm;
piperine up to 1 ppm, preferably between 0.3 and 0.5 ppm.

The composition of preferred feed additives, includes optionally other chemical compounds, for example at least one compound found in plants, and selected from the following group, as, per kg of feed,
up to about 1 mg of propylidene, butylidene, phtalides, gingerol, lavender oil;
up to about 2 mg of deca-, undeca-, dodecalactones, ionones, irone, resorcinol, eucalyptol, menthol, peppermint oil, alpha-pinene;
up to about 3 mg of limonene, guajacol, anethol, linalool, methyl dihydrojasmonate;
up to about 4 mg of carvacrol, propionic, acetic or butyric acid, rosemary oil, clove oil, geraniol, terpineol, citronellol;
up to about 5 mg of amyl and/or benzyl salicylate, cinnamaldehyde, vanilline, a plant polyphenol (tannin);
and up to about 5 mg of a powder of turmeric or of an extract of *curcuma*.

All these additional compounds may be used in combination with an emulsifying surfactant.

The emulsifying agent can be selected advantageously from those of a rather hydrophilic nature, for example among polyglycerol esters of fatty acids such as esterified ricinoleic acid or propylene glycol esters of fatty acids, saccharo-esters or saccharo-glycerides, polyethylene glycol, lecithins etc.

In a preferred embodiment of a poultry feeding concept, the feed additive includes benzoic aced and a mixture of thymol, eugenol and piperine; wherein these three compounds being used in amounts sufficient to provide a daily dosage of 0.1 mg to about 1 mg thymol and eugenol and of 0.02 mg to about 0.06 mg piperine per kg body weight of the subject to which it is to be administered.

The incorporation of the composition of feed additives as exemplified herein above to poultry feeds is in practice carried out using a concentrate or a premix. A premix designates a preferably uniform mixture of one or more micro-ingredients with diluent and/or carrier. Premixes are used to facilitate uniform dispersion of micro-ingredients in a larger mix. A premix according to the invention can be added to feed ingredients or to the drinking water as solids (for example as water soluble powder) or liquids.

A part from the compound mixture of the invention, animal feed additives of the invention contain at least one fat-soluble vitamin, and/or at least one water soluble vitamin, and/or at least one trace mineral, and/or at least one macro mineral.

Further, optional, feed-additive ingredients are coloring agents, e.g. carotenoids such as beta-carotene, astaxanthin, canthaxanthin, apoester and lutein; aroma compounds; stabilisers; antimicrobial peptides; polyunsaturated tatty acids (PUFAs); reactive oxygen generating species; and/or at least one enzyme selected from amongst phytase (EC 3.1.3.8 or 3.1.3.26); xylanase (EC 3.2.1.8); galactanase (EC 3.2.1.89); alpha-galactosidase (EC 3.2.1.22); protease (EC 3.4, phospholipase A1 (EC 3.1.1.32); phospholipase A2 (EC 3.1.1.4); lysophospholipase (EC 3.1.1.5); phospholipase C (EC 3.1.4.3); phospholipase D (EC 3.1.4.4); amylase such as, for example, alpha-amylase (EC 3.2.1.1); and/or beta-glucanase (EC 3.2.1.4 or EC 3.2.1.6).

Examples of antimicrobial peptides (AMP's) are CAP18, Leucocin A, Protegrin-1, Thanatin, Defensin, Lactoferrin, Lactoferricin, and Ovispirin such as Novispirin (Robert Lehrer, 2000), Plectasins, and Statins.

Examples of polyunsaturated fatty acids are C18, C20 and C22 polyunsaturated fatty acids, such as arachidonic acid, docosohexaenoic acid, eicosapentaenoic acid and gamma-linoleic acid.

Examples of reactive oxygen generating species are chemicals such as perborate, persulphate, or percarbonate; and enzymes such as an oxidase, an oxygenase or a syntethase.

Usually fat- and water-soluble vitamins, as well as trace minerals form part of a so-called premix intended for addition to the feed, whereas macro minerals are usually separately added to the feed.

The following are non-exclusive lists of examples of these components:
Examples of fat-soluble vitamins are vitamin A, vitamin D3, vitamin E, and vitamin K, e.g. vitamin K3.
Examples of water-soluble vitamins are vitamin B12, biotin and choline, vitamin B1, vitamin B2, vitamin B6, niacin, folic acid and panthothenate, e.g. Ca-D-panthothenate.
Examples of trace minerals are manganese, zinc, iron, copper, iodine, selenium, and cobalt.
Examples of macro minerals are calcium, phosphorus and sodium.

A premix can contain, for example, per ton of poultry feed, 50 to 200 g of a propylene glycol solution of the mixture of the active compounds, 20 to 1000 g of an emulsifying agent, 50 to 900 g of cereals and by-products, 20 to 100 g of a proteinic support (milk powder, casein, etc) and 50 to 300 g of a mineral component (expanded silica, feed quality lime, bi-calcium phosphate, etc).

Finally, the inventors surprisingly found that a feed additive composition comprising an organic acid, preferably benzoic acid, in combination with essential oil compounds shows good properties in regard to stability, content uniformity, tolerance and feedstuff utilization, if the essential oil compounds are adsorbed on a mineral carrier and blended with an adhering agent and the organic acid.

It is therefore a fifth aspect of the invention to provide a feed additive composition comprising an organic acid, a derivative or a metabolite thereof in combination with at least two essential oil compounds, wherein the essential oil compound(s) is/are adsorbed on a mineral carrier and blended with an adhering agent and the organic acid.

An important feature of the feed additive composition according to the invention is that the essential oil present in the composition is adsorbed on a mineral carrier, wherein the mineral carrier preferably belongs to the group consisting of silicon dioxide, aluminium and magnesium silicates and Kieselguhr, Another important feature of the feed additive composition is that an adhering agent is present in the composition which is responsible for adsorbing the essential oil compounds to the organic acid particles, wherein the adhering agent preferably belongs to the group consisting of vegetable oils as for example soya oil, waxes, molasses, poly ethylene glycol, pectin and derivatives of cellulose.

Just another important feature of the invention is that the essential oil compounds which are adsorbed on a mineral carrier are finally adsorbed via the adhering agent on the surface of the organic acid particles.

Preferably, at least one essential oil compound is selected from the group consisting of thymol, eugenol, eucalyptol, menthol, guajacol, carvacrol, geraniol, cinnamaldehyde vanilline, tannine and piperine and present in the composition in an amount of between 2% and 50% by weight of the composition. The organic acid is for example derived from citrate, succinate, benzoate, fumarate, L-asparate or L-malate and present in the composition in an amount of between 50% and 95% by weight.

A preferred example of such a feed additive composition comprises a mixture of at least two compounds selected from the group consisting of thymol, eugenol and piperine, which are adsorbed on the mineral carrier, preferably on a silicate. The composition is further blended with a vegetable oil, and benzoic acid.

In another preferred embodiment of the invention, the essential oil compounds may be blended with an emulsifying surfactant before the adsorption on the mineral carrier takes place. The emulsifying agent can be selected advantageously from those of a rather hydrophilic nature, for example polyglycerol esters of fatty acids such as esterified ricinoleic acid or propylene glycol esters of fatty acids, saccharo-esters or saccharo-glycerides, polyethylene glycol, lecithins etc.

In another preferred embodiment of the invention, the at least one essential oil compound or extract is present in an amount of between 5% to 20%, more preferably between 5 and 10% by weight of the composition, and the organic acid, preferably benzoic acid, is present in the composition in an amount of between 80% to 90%, more preferably between 80 and 85% by weight of the composition As aforementioned, thymol, eugenol and piperine are commercially available or can easily be prepared by a skilled person using processes and methods well-known in the prior art to and can be used in highly purified forms in mixtures or in the form of natural available plant extracts or extract-mixtures. This is also the case for all other essential oil compounds mentioned above.

Citric, fumaric and malic acids are commonly found in nature and are an intermediate of the tricarboxylic acid cycle (Krebs cycle). The Krebs cycle is a pathway for degradation of carbohydrates and generation of energy in humans and animals. These organic acids are also associated with growth of prominent ruminal bacteria.

Aspartic acid is a non essential amino acid and can be manufactured from other amino acids in the liver. Aspartate is required for growth of microorganism in the rumen and cecum. Aspartic acid is also very important in the urea cycle for the proper elimination of waste products from dietary protein.

In the scope of the feed additive composition defined hereinabove, it should be noted that the essential oils and organic acids listed above are representative of the preferred types of compounds to be used in the feed additive, but the composition may be composed of other types of essential oils and organic acids so long as the essential oils and organic acids promote growth and/or improve feed conversion of the animals consuming the feed additive.

Finally, the incorporation of the feed additive composition to animal feed is in practice carried out using a concentrate or a premix as described herein above.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

EXAMPLES

The following examples further illustrate the invention.

Example 1

A broiler chicken feed ("starter") containing a mixture of compounds according to the invention can be prepared by mixing the following ingredients together using a conventional mixing apparatus at room temperature.

| Ingredient | Amount (kg) |
| --- | --- |
| Soybean meal | 34.50 |
| Maize | 20.00 |
| Wheat | 37.80 |
| Soy oil | 3.13 |
| Minerals | 2.90 |
| Synthetic amino acids premix | 0.17 |
| Vitamins and trace elements premix | 1.00 |
| thymol | 5 mg |
| eugenol | 2 mg |
| piperine | 0.35 mg |
| turmeric powder | 3 mg |
| benzoic acid | 250 mg |

Example 2

A broiler chicken feed ("grower") containing a mixture of compounds according to the invention can be prepared by mixing the following ingredients together using a conventional mixing apparatus at room temperature.

| Ingredients | Amount (kg) |
| --- | --- |
| Soybean meal | 31.2 |
| Maize | 20.0 |
| Wheat | 41.3 |
| Soy oil | 3.4 |
| Minerals | 2.5 |
| Synthetic amino acids premix | 0.1 |
| Vitamins and trace elements premix | 1.0 |
| thymol | 5 mg |
| eugenol | 2 mg |
| piperine | 0.35 mg |
| benzylsalicylate | 5 mg |
| turmeric powder | 3 mg |
| benzoic acid | 250 mg |

Example 3

Evaluation of the Effects of Different Combinations of a Composition Comprising at Least a Mixture of Thymol, Eugenol and Piperine with Benzoic Acid (VevoVitall) on the Growth Performance of Broiler Chickens Over Three Weeks A growth performance trial with broiler chickens was performed from day 8 to day 29. The chickens were housed in wire-floored battery cages. From day-old until day 8, the chickens were fed a pre-experimental diet based on wheat, maize and soybean meal. In the experimental period (day 8 to 29) the chickens received diets based on wheat, rye and soybean meal (composition see Table 1). Groups of birds were weighed on days 8, 15, 22 and 29. The feed consumption for the intermediate periods was determined and body weight gain and feed conversion ratio were calculated.

Beside an un-supplemented control treatment and a positive control containing 10 mg of the antibiotic Avilamycin per kg feed, benzoic acid (VevoVitall) was included at 500 mg per kg feed. In addition, per kg feed, combinations of 250 mg benzoic acid and 50 mg of the composition comprising thymol, eugenol and piperine (herein abbreviated by TEP) as well as either 500 mg benzoic acid and 25 mg TEP or 500 mg benzoic acid and 50 mg TEP were tested, respectively.

At a combination of 250 mg benzoic acid with 50 mg TEP per kg feed, weight gain was improved by 4.2% compared to the control. VevoVitall alone at a dose of 500 mg/kg improved weight gain by 3% compared to the control. A combination of 500 mg benzoic acid and 25 mg TEP per kg feed resulted in #4.8% weight gain. The highest improvements in weight gain were found for the antibiotic Avilamycin (+8.7%) and for the combination of 500 mg benzoic acid and 50 mg TEP (+11.2%) (Table 2). For feed conversion (FCR), the positive effects of the combination of 250 mg benzoic acid with 50 mg TEP were in the same range as those of the positive control supplemented with the antibiotic Avilamycin (4.3% compared to the negative control). Highest improvement of FCR was found for the treatment supplemented with 500 mg benzoic acid plus 50 mg TEP (10.2%).

The results of the present trial demonstrate that the different combinations of benzoic acid and TEP were effective in improving the growth performance of chickens fed diets based on wheat, rye and soybean meal over three weeks.

Experimental Plan

| | |
| --- | --- |
| Growth trial: | day 8 to day 29 (pre-experimental period from day 1 to day 8) |
| Diets: | wheat/rye/SBM48 diet (see feed composition) |
| Feeding: | pellets ad libitum |
| Treatments: | Control |
| | Avilamycin (10 mg/kg) |
| | Benzoic acid (250 mg/kg) + TEP composition (50 mg/kg) |
| | Benzoic acid (500 mg/kg) |
| | Benzoic acid (500 mg/kg) + TEP composition (25 mg/kg) |
| | Benzoic acid (500 mg/kg) + TEP composition (50 mg/kg) |
| Replicates: | 6 groups of 6 male chickens (ROSS PM3) per treatment |
| Housing: | wire-floored battery cages in an environmentally controlled room |
| Products: | Avilamycin, Maxus G 200 Benzoic acid, VevoVitall, DSM Nutritional Products AG TEP composition comprises as main ingredients the following compounds, wherein these compounds are blended on a vegetable and mineral carrier comprising wood fibre, wheat semolina, silicon dioxide and calcium carbonate: |

-continued

| Ingredients | % (w/w) |
| --- | --- |
| Thymol | 10 |
| Turmeric powder | 3 |
| Eugenol | 4 |
| Badiane | 0.8 |
| Piperine | 0.7 |

TABLE 1

Feed composition of the experimental diet

| Ingredients (%): | Pre-experimental period | Growth trial |
| --- | --- | --- |
| Maize | 37.10 | — |
| Wheat | 20.00 | 27.30 |
| Rye | — | 30.00 |
| SBM 48 | 36.20 | 34.20 |
| Soybean oil | 2.80 | 4.50 |
| DL-Methionine | 0.20 | 0.20 |
| DCP | 1.80 | 2.00 |
| Limestone | 0.80 | 0.70 |
| Salt | 0.10 | 0.10 |
| Premix | 1.00 | 1.00 |

TABLE 2

Performance of broiler chickens over the growth cycle (day 8 to day 29)

| Product | Control | Avilamycin | VevoVitall + TEP composition | VevoVitall | VevoVitall + TEP composition | |
| --- | --- | --- | --- | --- | --- | --- |
| Dose (mg/kg) | — | 10 | 250 + 50 | 500 | 500 + 25 | 500 + 50 |
| cages × birds | 6 × 6 | 6 × 6 | 6 × 6 | 6 × 6 | 6 × 6 | 6 × 6 |
| Day 8-29 | | | | | | |
| Weight gain (g/bird) | 1160 ± 63.6<br>100.0 | 1261 ± 76.8<br>108.7 | 1209 ± 101.4<br>104.2 | 1196 ± 103.0<br>103.1 | 1216 ± 119.9<br>104.81 | 1291 ± 40.3<br>111.2 |
| Feed intake (g/bird) | 2433 ± 233.1<br>100.0 | 2533 ± 199.6<br>104.1 | 2417 ± 237.1<br>99.4 | 2538 ± 309.6<br>104.3 | 2559 ± 382.0<br>105.2 | 2432 ± 120.4<br>100.0 |
| Feed conversion (g feed/g gain) | 2.099 ± 0.197<br>100.0 | 2.008 ± 0.052<br>95.7 | 2.006 ± 0.187<br>95.6 | 2.117 ± 0.093<br>100.8 | 2.106 ± 0.262<br>100.3 | 1.885 ± 0.083<br>89.8 |

Example 4

Evaluation of Antimicrobial Activity of Compositions According to the Invention

Starting from a glycerol stock, a pre-culture of *E. coli* and *Clostridium perfringens* were performed in 10 ml Tryptic Soy Broth (TSB, Merck) at 37° C., shaking at 250 rpm over-night. These precultures were diluted in TSB to get a bacterial suspension with approximately $4 \times 10^4$ cfu/ml. VevoVitall and the composition TEP as specified in example 3 were dissolved and added to the bacterial suspension.

At time zero the $OD_{595\ nm}$ was measured to take into account any turbidity due to precipitated compounds. The plates were then incubated over night at 37° C. in a humid atmosphere and shaken at 200 rpm in anaerobiosis. After 24 hours the OD595 nm was measured to calculate the percent inhibition.

The results are shown in FIG. 1 (*Clostridium perfringens*) and 2 (*Escherichia coli*), wherein vertical axis of both figures show "Growth inhibition (% of control)" and the horizontal axis of both figures show "Content of compound indicated as equivalent contents of the total mixture of the invention"

Example 5

Preparation of a Dry Feed Additive 50 g of Kieselguhr are added to a beaker and 10 g of eugenol and 1 g of rosemary oil are slowly dropped on the mineral and slowly stirred. 500 g of benzoic acid is added to a Turbula mixer and 10 g of hardened palm oil warmed to 60° C. is sprayed on the acid and slowly mixed for 5 minutes, 50 g of the essential oil containing mineral is then added and blended for 10 minutes, to obtain a uniform dry powder.

The invention claimed is:

1. A method for improving feed conversion ratio and/or daily weight gain and/or gut flora modulation in poultry, which method comprises providing to poultry for ingestion a feed which comprises benzoic acid in an effective amount from 50 to 1000 mg/kg of feed in combination with a mixture of at least two active compounds selected from the group consisting of thymol, eugenol and piperine.

2. A method for improving feed conversion ratio and/or daily weight gain and/or gut flora modulation and/or as antimicrobial agent in poultry, which method comprises providing to poultry for ingestion a feed which comprises benzoic acid in an effective amount from 50 to 1000 mg/kg of feed in combination with a mixture of at least two active compounds selected from the group consisting of thymol, eugenol and piperine.

3. The method according to claim 2, which further comprises co-feeding of poultry with a composition comprising the benzoic acid as a main ingredient together with a composition comprising a mixture of at least two compounds selected from the group consisting of thymol, eugenol and piperine.

4. The method according to claim 1, wherein said mixture comprises thymol, eugenol and piperine.

5. The method according to claim 1, wherein said mixture comprises at least one additional chemical compound selected from the group consisting of propylidene, butylidene, phtalides, gingerol, lavender oil, deca-, undeca-, dodecalactones, ionones, irone, resorcinol, eucalyptol, menthol, peppermint oil, alpha-pinene, limonene, guajacol, anethol, linalool, methyl dihydrojasmonate, carvacrol, propionic, acetic or butyric acid, rosemary oil, clove oil, geraniol, terpineol, citronellol, amyl and/or benzyl salicylate, cinnamaldehyde, vanilline, plant polyphenol, powder of turmeric, extract of curcuma.

6. The method according to claim 1, wherein said benzoic acid is present in the feed in an amount sufficient to provide a daily dosage of 5 mg per kg body weight to about 80 mg per kg body weight of the poultry to which it is administered.

7. The method according to claim 1, wherein, thymol, eugenol and piperine are present in the feed in amounts sufficient to provide a daily dosage of 0.5 mg to about 1 mg thymol and eugenol and of 0.02 mg to about 0.06 mg piperine per kg body weight of the poultry to which it is administered.

8. A method for improving feed conversion ratio and/or daily weight gain and/or gut flora modulation in poultry, which method comprises providing to poultry for ingestion a feed which comprises benzoic acid in an effective amount from 50 to 1000 mg/kg of feed in combination with a mixture of at least two active compounds selected from the group consisting of thymol, eugenol and piperine, which are present as ingredients of the feed ingested by the poultry.

9. A method according to claim 1 or 8, wherein the poultry is one selected from chickens, turkeys and ducks.

10. A method as in claim 9, wherein the poultry is selected from broiler and layer chickens.

* * * * *